United States Patent [19]
Chen et al.

[11] Patent Number: 5,745,239
[45] Date of Patent: Apr. 28, 1998

[54] MULTIPLE FOCAL PLANE IMAGE COMPARISON FOR DEFECT DETECTION AND CLASSIFICATION

[75] Inventors: Bor-Cheng Chen, Taipei; Yeh-Jye Wann, Hsin-chu, both of Taiwan

[73] Assignee: Taiwan Semiconductor Manufacturing Company, Hsin-chu, Taiwan

[21] Appl. No.: 826,713

[22] Filed: Apr. 7, 1997

[51] Int. Cl.⁶ .................................. G01B 11/28
[52] U.S. Cl. .................. 356/380; 356/386; 356/376; 356/372
[58] Field of Search .................... 356/380, 386, 356/376, 372

[56] References Cited

U.S. PATENT DOCUMENTS

| | | | |
|---|---|---|---|
| 4,468,120 | 8/1984 | Tanimoto et al. | 356/237 |
| 4,889,998 | 12/1989 | Hayano et al. | 356/237 |
| 4,966,457 | 10/1990 | Hayano et al. | 356/237 |
| 5,177,559 | 1/1993 | Batchelder et al. | 356/237 |
| 5,185,812 | 2/1993 | Yamashita et al. | 382/8 |
| 5,204,910 | 4/1993 | Lebeau | 382/8 |
| 5,293,538 | 3/1994 | Iwata et al. | 356/237 |
| 5,317,380 | 5/1994 | Allemand | 356/338 |
| 5,513,275 | 4/1996 | Khalaj et al. | 382/149 |
| 5,515,163 | 5/1996 | Kupershmidt et al. | 356/338 |

*Primary Examiner*—Frank G. Font
*Assistant Examiner*—Reginald A. Ratliff
*Attorney, Agent, or Firm*—George O. Saile; Stephen B. Ackerman; Larry J. Prescott

[57] ABSTRACT

An apparatus and method of analyzing particles on an integrated circuit wafer using a quasi three dimensional image analysis of the particles. The apparatus includes an optical system which has an optical axis and forms an image of that part of a focal plane which within a field distance of the optical axis. The apparatus holds a wafer perpendicular to the optical axis and allows the surface of the wafer to be moved in a plane perpendicular to the optical axes to view the entire surface of the wafer. The apparatus also allows the surface of the wafer to be moved a step distance below the focal plane. Images formed at a number of step distances are used to form a quasi three dimensional image of particles on the surface of the wafer. Automatic image analysis is used when appropriate.

19 Claims, 4 Drawing Sheets

MULTIPLE FOCAL PLANE IMAGE COMPARISON FOR DEFECT DETECTION AND CLASSIFICATION

BACKGROUND OF THE INVENTION (1) Field of the Invention

This invention relates to a quasi thee dimensional image analysis of surface defects on integrated circuit wafers and more particularly to the analysis of images formed in multiple focal planes above the wafer surface for defect detection and classification.

(2) Description of the Related Art

U.S. Pat. No. 5,515,163 to Kuperschmidt et al. describes a method and apparatus for the analysis of particles on a wafer using two orthogonally polarized intensity and phase modulated laser beams.

U. S. Pat. No. 5,317,380 to Allemand shows a particle detection method and apparatus using a scanning beam of laser light brought to focus as an accurate scan line on a surface of the object at a grazing angle of incidence.

U.S. Pat. No. 5,185,812 to Yamashita et al. describes a pattern inspection apparatus using a two dimensional inspected pattern as image data for comparison of the image data with reference data.

U.S. Pat. No. 5,513,275 to Khalaj et al. describes a self-reference signal processing technique for detecting the location of any non-regularities and defects in a periodic two dimensional signal or image.

U.S. Pat. No. 5,204,910 to Lebeau describes a method of image processing for visually inspecting a workpiece. The method compares the brightness at each location within an image of the workpiece to the equivalent location within an image of an idealized workpiece.

U.S. Pat. No. 5,293,538 to Iwata describes an inspection method and apparatus to detect a defect on the surface of a protection layer or a defect in the protection layer through detection of light derived from an illumination light. An image process which images two elements having the same appearance compares the two images using bright field illumination and bright/dark field illumination to compare the two images.

U.S. Pat. No. 5,177,559 to Batchelder et al. describes an optical inspection system for a patterned wafer which generates a dark field image of the wafer using light at an eight degree angle of incidence and collecting light scattered at angles approximately normal to the wafer surface.

The invention described in this patent application comprises an apparatus and method of analyzing a wafer surface for defects using a quasi three dimensional analysis of the wafer surface. Images taken at focal planes at various distances above the wafer surface provide three dimensional information for the analysis.

SUMMARY OF THE INVENTION

In the manufacture of integrated circuit wafers it is necessary to inspect the surface of the wafers at various points in the manufacturing process to determine if defects are present or if particles of dust, debris, or other contamination are present. This inspection is an optical inspection and automated means are used whenever possible. Conventional methods of optical inspection use a two dimensional observation of the surface of the wafer. Two dimensional observations of surface defects can be quite misleading. Particulate contaminants which are quite different can appear much the same, if not identical, in a two dimensional optical analysis of the surface. Information regarding the third dimension, that perpendicular to the wafer surface, can be very important in understanding, and thereby controlling, surface contamination.

It is a principle objective of this invention to provide a method of optically inspecting and analyzing substrate surfaces using information from three dimensions, perpendicular to the wafer surface as well as parallel to the wafer surface.

It is a another principle objective of this invention to provide apparatus for optically inspecting and analyzing substrate surfaces using information from three dimensions, perpendicular to the wafer surface as well as parallel to the wafer surface.

These objectives are achieved by using an optical system which can be focussed at focal planes which are parallel to the surface of the substrate under analysis and at a pre determined step distance above the substrate surface. Images taken at focal planes located at a number of step distances above the substrate surface provide a quasi three dimensional image of any objects located on the substrate. This quasi three dimensional analysis can be automated so that images at various step heights of objects located on the substrate can be compared with expected images.

DESCRIPTION OF THE PREFERRED EMBODIMENTS

Figure 1:
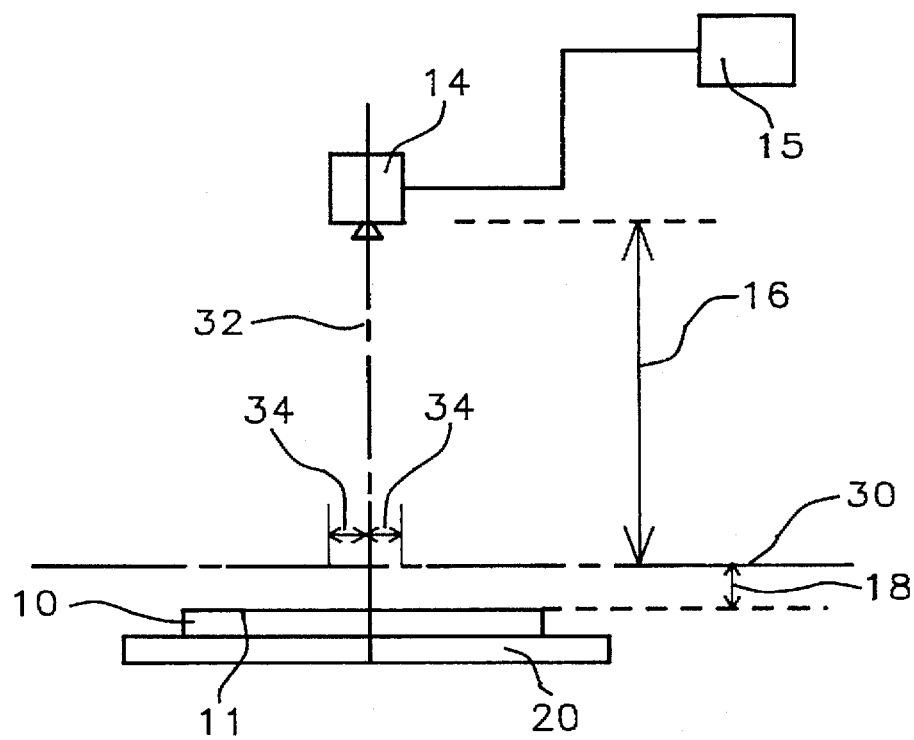
FIG. 1 shows a block diagram of an optical system used for quasi three dimensional analysis of a wafer surface.

Refer to FIGS. 1-5D for a detailed description of the method and apparatus of this invention for the inspection of wafer surfaces. FIG. 1 shows a block diagram of the inspection apparatus used to inspect the wafer surface. The inspection apparatus includes an optical system 14 which may be a visual inspection system, such as a microscope, or may be an electronic imaging system, such as a CCD image display, which can be sent directly to an image analysis system 15 for automatic analysis of the image. The automatic image analysis system 15 can, for example, compare the image formed by the optical system 14 with an expected image including a comparison of such image parameters as image density and color. The optical system 14 has an optical axis 32 and a focal plane 30. The optical system 14 forms an image of that part of the focal plane 30 within a field image distance 34 of the optical axis 32.

The inspection apparatus has a wafer holder 20 for holding a wafer 10 to be inspected so that the first surface 11 of the wafer 10, the surface being inspected, is perpendicular to the optical axis 32. The wafer holder 20 can move the first surface 11 of the wafer 10 in a plane perpendicular to the optical axis 32 so that the entire first surface 11 of the wafer 10 can be inspected. The focal plane 30 is located a step distance 18 above the first surface 11 of the wafer 10. The wafer holder 20 can also move the first surface 11 of the wafer 10 in a direction parallel to the optical axis 32 so that the step distance 18 can be varied. In all movements of the wafer holder 20 the first surface 11 of the wafer 10 remains perpendicular to the optical axis 32 and therefor parallel to the focal plane 30. The step distance can be any distance useful for analysis of the first surface 11 of the wafer 10 and, in this example, is between about zero and ten micrometers.

Figure 2:
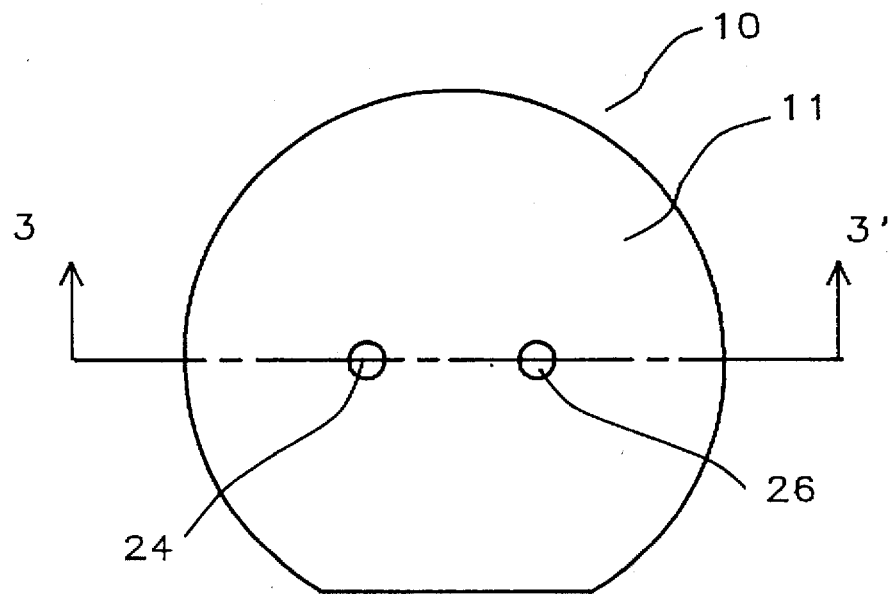
FIG. 2 shows a top view of a wafer showing two unwanted objects on the wafer surface.
Figure 3:
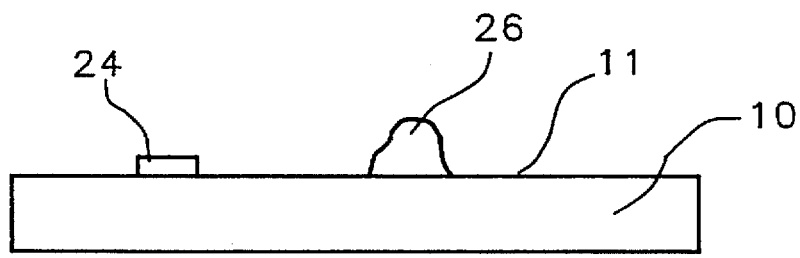
FIG. 3 shows a cross sectional view of the wafer of FIG. 2 showing a cross section view of the two unwanted objects on the wafer surface.

FIG. 2 shows a top view of a wafer 10 to be inspected. FIG. 2 shows a first particle 24 and a second particle 26 on the first surface 11 of the wafer. In the top, or two dimensional, view of the particles the first particle 24 and the second particle 26 look very much alike. FIG. 3 shows a cross section view of the wafer 10 along the line 3—3' of FIG. 2. FIG. 3 shows that the first particle 24 and the second particle 26 are very different. This difference is very apparent using the quasi three dimensional image analysis of this invention.

Figure 4A:
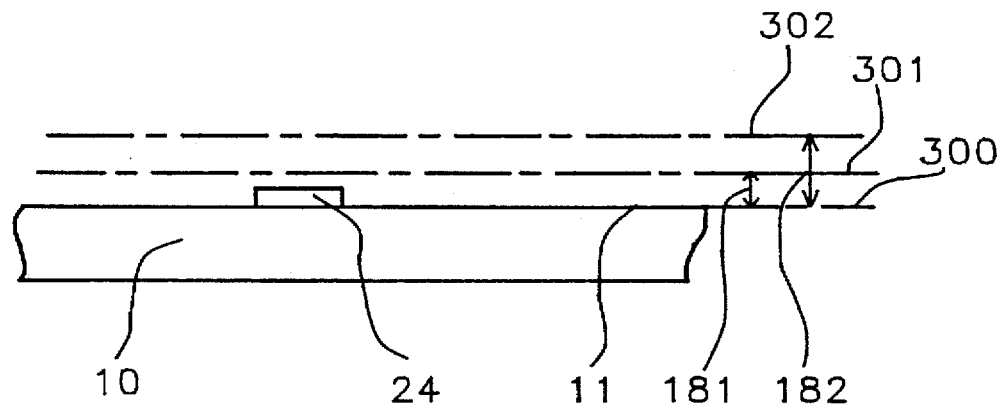
FIG. 4A shows a cross section view of a portion of a wafer showing a first unwanted object on the wafer surface.

The method of quasi three dimensional image analysis of this invention is shown in FIGS. 4A–5D. FIG. 4A shows a cross section view of the first particle 24. A first image, 240 in FIG. 4B, of the first particle 24 is formed with the focal plane 300 at the first surface 11 of the wafer 10. A second image, 241 in FIG. 4C, of the first particle 24 is formed with the focal plane 301 at a first step distance 181 above the first surface 11 of the wafer. A third image, see FIG. 4D, of the first particle 24 is formed with the focal plane 302 at a second step distance 182, larger than the first step distance, above the first surface 11 of the wafer. The first, second, and third images are then analyzed by comparison with expected images and each other. Either automated or manual image analysis can be used.

Figure 4B:
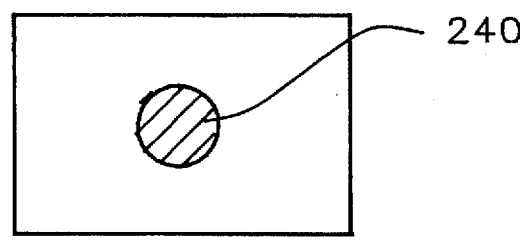
FIG. 4B shows an image of the portion of the wafer shown in FIG. 4A at a first distance above the surface of the wafer.
Figure 4C:
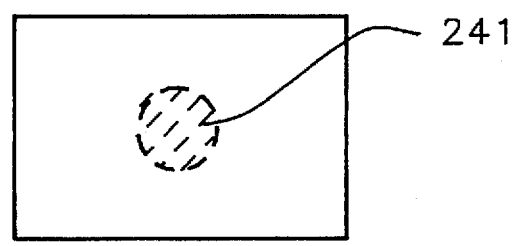
FIG. 4C shows an image of the portion of the wafer shown in FIG. 4A at a second distance above the surface of the wafer.
Figure 4D:
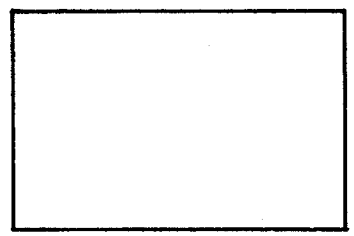
FIG. 4D shows an image of the portion of the wafer shown in FIG. 4A at a third distance above the surface of the wafer.

As shown in FIGS. 4A and 4B, the first image 240 of the first particle 24 shows an image of the outline of the first particle 24 on the first surface 11 of the wafer. As shown in FIGS. 4A and 4C, the second image 241 of the first particle 24 shows a slightly out of focus image of the outline of the first particle 24 since at the first step distance 181, the focal plane 301 is slightly above the top of the first particle 24. As shown in FIGS. 4A and 4D, no image of the first particle 24 is formed when the focal plane 302 is at the second step distance 182 since at this step distance 182 the focal plane 302 is too far above the top of the first particle 24 to form an image.

Figure 5A:
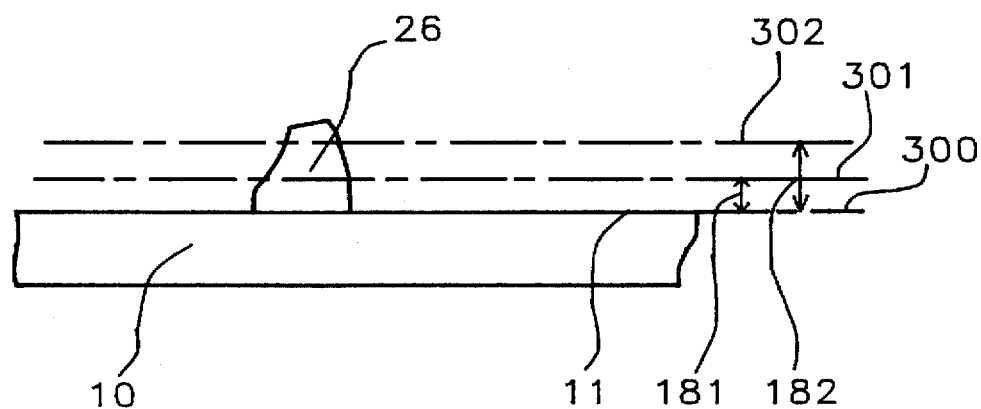
FIG. 5A shows a cross section view of a portion of a wafer showing a second unwanted object on the wafer surface.

FIG. 5A shows a cross section view of the second particle 26. A first image, 260 in FIG. 5B, of the second particle 26 is formed with the focal plane 300 at the first surface 11 of the wafer. A second image, 261 in FIG. 5C, of the second particle 26 is formed with the focal plane 301 at a first step distance 181 above the first surface 11 of the wafer. A third image, see FIG. 5D, of the second particle 26 is formed with the focal plane 302 at a second step distance 182, larger than the first step distance, above the first surface 11 of the wafer. The first, second, and third images are then analyzed by comparison with expected images and each other. Either automated or manual image analysis can be used.

Figure 5B:
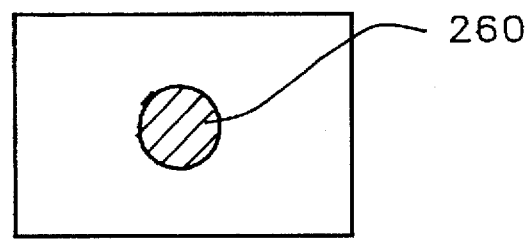
FIG. 5B shows an image of the portion of the wafer shown in FIG. 5A at a first distance above the surface of the wafer.
Figure 5C:
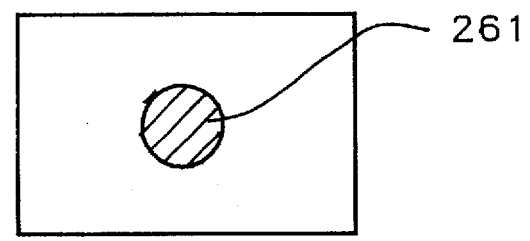
FIG. 5C shows an image of the portion of the wafer shown in FIG. 5A at a second distance above the surface of the wafer.
Figure 5D:
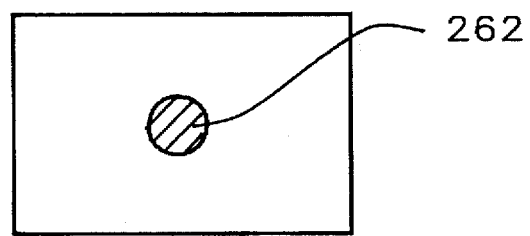
FIG. 5D shows an image of the portion of the wafer shown in FIG. 5A at a third distance above the surface of the wafer.

As shown in FIGS. 5A and 5B, the first image 260 of the second particle 26 shows an image of the outline of the second particle 24 on the first surface 11 of the wafer. As shown in FIGS. 5A and 5C, the second image 261 of the second particle 26 is an image of the outline of the intersection of the second particle 24 and the focal plane 301 located at the first step distance 181. As shown in FIGS. 5A and 5D, the third image 262 of the second particle 26 is an image of the outline of the intersection of the second particle 26 and the focal plane 302 located at the second step distance 182.

This example has used three step distances to analyze the first particle 24 and the second particle 26 on the first surface 11 of the wafer. It will be readily apparent to those skilled in the art that a smaller or greater number of step distances can be used as the nature of the analysis may require.

It is easily seen from the images of the first particle 24, FIGS. 4B–4D, and the second particle 26, FIGS. 5B–5D, that the image formed in the focal plane 300 at the first surface of the wafer 11 look very similar; but that the images formed in focal planes, 301 and 302, located at a first step height 181 and a second step height 182 above the first surface of the wafer 11 look very different. A two dimensional analysis would not be able to distinguish between the first particle 24 and the second particle 26. The quasi three dimensional analysis of this invention easily distinguished between the first particle 24 and the second particle 26.

While the invention has been particularly shown and described with reference to the preferred embodiments thereof, it will be understood by those skilled in the art that various changes in form and details may be made without departing from the spirit and scope of the invention.

What is claimed is:

1. A method of optical analysis, comprising the steps of:

providing an optical system having an optical axis and a focal plane wherein said optical axis is perpendicular to said focal plane and said optical system forms an image of that part of said focal plane within an image field distance of said optical axis;

providing means to analyze each said image formed by said optical system;

providing means for holding a substrate having a primary surface so that said primary surface is parallel to said focal plane, a step distance away from said focal plane, and perpendicular to said optical axis;

providing means for varying said step distance;

providing means for varying the position at which said optical axis intersects said primary surface;

setting said position at which said optical axis intersects said primary surface at an analysis position;

setting a characteristic number of said step distances for each of said analysis positions;

forming one said image for each of said step distances at each of said analysis positions, thereby forming said characteristic number said images at each of said analysis positions; and analyzing said characteristic number of said images for each of said analysis positions.

2. The method of claim 1 wherein said substrate having a primary surface is a semiconductor substrate.

3. The method of claim 2 wherein said semiconductor substrate has integrated circuit devices formed therein.

4. The method of claim 1 wherein said characteristic number is three.

5. The method of claim 1 wherein said step distance is between about 0 and 10 micrometers.

6. The method of claim 1 wherein said analyzing said characteristic number of said images at each of said analysis positions comprises comparison of each said image with an expected image.

7. The method of claim 1 wherein said analyzing characteristic number of said images at each of said analysis positions comprises a comparison of the density of each said image with a threshold image density.

8. The method of claim 1 wherein said analyzing said characteristic number of said images at each of said analysis positions comprises a comparison of the color content of each said image with an expected color content.

9. The method of claim 1 wherein said analyzing said characteristic number of said images at each of said analysis positions comprises a comparison of each said image with every other said image at each of said analysis positions.

10. The method of claim 1 wherein said analyzing said characteristic number of said images at each of said analysis positions comprises an automated analysis of said images.

11. An apparatus for analyzing particles on a substrate, comprising:

an optical system having an optical axis and a focal plane wherein said optical axis is perpendicular to said focal plane and said optical system forms an image of that part of said focal plane within an image field distance of said optical axis;

means for holding a substrate having a primary surface so that said primary surface of said substrate is parallel to said focal plane, a step distance away from said focal plane, and perpendicular to said optical axis;

means for varying said step distance;

means for varying the position at which said optical axis intersects said primary surface; and means to analyze each said image formed by said optical system.

12. The apparatus of claim 11 wherein said substrate having a primary surface is a semiconductor substrate.

13. The apparatus of claim 12 wherein said semiconductor substrate has integrated circuit devices formed therein.

14. The apparatus of claim 11 wherein said step distance is between about 0 and 10 micrometers.

15. The apparatus of claim 11 wherein said means to analyze each said image comprises a comparison of each said image with an expected image.

16. The apparatus of claim 11 wherein said means to analyze each said image comprises a comparison of the density of each said image with a threshold image density.

17. The apparatus of claim 11 wherein said means to analyze each said image comprises a comparison of the color content of each said image with an expected color content.

18. The apparatus of claim 11 wherein said means to analyze each said image comprises a comparison of each said image with other said images.

19. The apparatus of claim 11 wherein said means to analyze each said image comprises an automated analysis of said image.

* * * * *